United States Patent
Okumura et al.

(10) Patent No.: US 10,918,454 B2
(45) Date of Patent: Feb. 16, 2021

(54) GASTROINTESTINAL TRACT CONSTRICTING METHOD

(71) Applicant: OLYMPUS CORPORATION, Tokyo (JP)

(72) Inventors: Takuya Okumura, Tokyo (JP);
Shunsuke Motosugi, Tokyo (JP);
Hiroyuki Morishita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 98 days.

(21) Appl. No.: 15/942,617

(22) Filed: Apr. 2, 2018

(65) Prior Publication Data
US 2019/0298476 A1 Oct. 3, 2019

(51) Int. Cl.
*A61B 90/00* (2016.01)
*A61B 17/00* (2006.01)
(Continued)

(52) U.S. Cl.
CPC ............ *A61B 90/04* (2016.02); *A61B 1/2736* (2013.01); *A61B 17/00234* (2013.01);
(Continued)

(58) Field of Classification Search
CPC ... A61B 90/04; A61B 17/3478; A61B 1/2736; A61B 17/00234; A61B 2017/0082; A61B 2017/0034; A61B 2090/0427; A61B 17/0469; A61B 17/320016; A61B 17/0218; A61B 17/12013; A61B 2090/0409;
(Continued)

(56) References Cited

U.S. PATENT DOCUMENTS 5,645,560 A 7/1997 Crocker et al.
5,843,116 A 12/1998 Crocker et al.
(Continued)

FOREIGN PATENT DOCUMENTS

EP 2 298 250 A1 3/2011
EP 3 141 192 A1 3/2017
(Continued)

OTHER PUBLICATIONS

Office Action dated Apr. 16, 2020 received in U.S. Appl. No. 15/704,198.

*Primary Examiner* — Kevin C Sirmons
*Assistant Examiner* — Antarius S Daniel
(74) *Attorney, Agent, or Firm* — Scully, Scott, Murphy & Presser, P.C.

(57) ABSTRACT

A gastrointestinal-tract constricting method comprises: while observing the gastrointestinal tract with an endoscope inserted into the gastrointestinal tract, placing a protection substance, which does not damage tissue, in at least one of a region between the mucosal layer and muscular layer of the gastrointestinal tract and a region in a mucosal surface of the mucosal layer so as to form a protection region that protects the mucosa basal layer from a medical substance that damages the tissue; and, after forming the protection region, supplying the medical substance to a mucosal surface in a target region, which is at a position different from the protection region in a circumferential direction of the gastrointestinal tract, or to a position between the mucosal layer and the muscular layer.

20 Claims, 12 Drawing Sheets

B-B' SECTION
(TRANSVERSE SECTION)

(51) Int. Cl.
*A61B 1/273* (2006.01)
*A61B 17/34* (2006.01)
*A61K 31/045* (2006.01)
*A61K 31/728* (2006.01)

(52) U.S. Cl.
CPC ........ *A61B 17/3478* (2013.01); *A61K 31/045* (2013.01); *A61K 31/728* (2013.01); *A61B 2017/0034* (2013.01); *A61B 2017/00827* (2013.01); *A61B 2090/0427* (2016.02)

(58) Field of Classification Search
CPC .... A61B 1/273; A61B 1/2733; A61K 31/728; A61K 31/045; A61M 2037/0023; A61M 2037/0061; A61M 2039/0279; A61M 37/0015; A61M 31/002; A61M 2210/1064; A61M 2210/1046; A61M 2210/105; A61M 2210/1057; A61M 2210/106; A61M 2210/1042; A61M 2210/1053; A61M 2202/0484; A61M 25/0084; A61M 2025/0089; A61M 2025/0091; A61M 5/00; A61M 5/46; A61M 37/002; A61F 5/0069; A61F 5/0013
See application file for complete search history.

(56) References Cited

U.S. PATENT DOCUMENTS

| | | | |
|---|---|---|---|
| 6,027,486 A | 2/2000 | Crocker et al. | |
| 6,098,629 A | 8/2000 | Johnson et al. | |
| 6,338,345 B1 | 1/2002 | Johnson et al. | |
| 6,401,718 B1 | 6/2002 | Johnson et al. | |
| 6,488,653 B1 | 12/2002 | Lombardo | |
| 6,500,174 B1 | 12/2002 | Maguire et al. | |
| 6,544,226 B1 | 4/2003 | Gaiser et al. | |
| 6,575,896 B2 * | 6/2003 | Silverman | A61B 17/12022 600/29 |
| 7,185,657 B1 | 3/2007 | Johnson et al. | |
| 2002/0148475 A1 | 10/2002 | Johnson et al. | |
| 2002/0198521 A1 | 12/2002 | Maguire | |
| 2003/0183962 A1 | 10/2003 | Buiser et al. | |
| 2003/0233150 A1 | 12/2003 | Boume et al. | |
| 2003/0236535 A1 | 12/2003 | Onuki et al. | |
| 2004/0087936 A1 * | 5/2004 | Stern | A61B 18/1492 606/41 |
| 2005/0096673 A1 | 5/2005 | Stack et al. | |
| 2005/0247320 A1 | 11/2005 | Stack et al. | |
| 2006/0247610 A1 * | 11/2006 | Lanphere | A61L 27/3683 606/21 |
| 2007/0060932 A1 | 3/2007 | Stack et al. | |
| 2007/0135822 A1 | 6/2007 | Onuki et al. | |
| 2007/0260112 A1 | 11/2007 | Rahmani | |
| 2007/0260178 A1 | 11/2007 | Skerven et al. | |
| 2007/0276432 A1 | 11/2007 | Stack et al. | |
| 2008/0015523 A1 | 1/2008 | Baker et al. | |
| 2008/0065122 A1 | 3/2008 | Stack et al. | |
| 2009/0018602 A1 | 1/2009 | Mitelberg et al. | |
| 2009/0240105 A1 * | 9/2009 | Smit | A61B 17/00491 600/104 |
| 2010/0168512 A1 | 7/2010 | Rahmani | |
| 2010/0174306 A1 | 7/2010 | Mitelberg et al. | |
| 2010/0217151 A1 | 8/2010 | Gostout et al. | |
| 2010/0241146 A1 | 9/2010 | Stack et al. | |
| 2011/0038938 A1 * | 2/2011 | Ison | A61L 27/46 424/489 |
| 2011/0257622 A1 * | 10/2011 | Salahieh | A61M 25/0074 604/500 |
| 2012/0095395 A1 | 4/2012 | Haery | |
| 2012/0226300 A1 | 9/2012 | Mitelberg et al. | |
| 2012/0226302 A1 | 9/2012 | Mitelberg et al. | |
| 2013/0012863 A1 | 1/2013 | Stack et al. | |
| 2013/0197554 A1 | 8/2013 | Skerven et al. | |
| 2013/0345670 A1 | 12/2013 | Rajagopalan et al. | |
| 2014/0010847 A1 * | 1/2014 | Lin | A61K 31/728 424/278.1 |
| 2014/0121585 A1 | 5/2014 | Baker et al. | |
| 2014/0249465 A1 | 9/2014 | Stack et al. | |
| 2015/0025313 A1 | 1/2015 | Baker et al. | |
| 2015/0032087 A1 | 1/2015 | Shibata et al. | |
| 2015/0157358 A1 | 6/2015 | Mitelberg et al. | |
| 2015/0352334 A1 | 12/2015 | Haery | |
| 2015/0374352 A1 * | 12/2015 | Inoue | A61F 5/0083 128/898 |
| 2016/0213890 A1 | 7/2016 | Kaufman et al. | |
| 2016/0262867 A1 | 9/2016 | Baker et al. | |
| 2016/0296675 A1 * | 10/2016 | Longo | A61B 1/018 |
| 2016/0310200 A1 | 10/2016 | Wang | |
| 2017/0035595 A1 | 2/2017 | Stack et al. | |
| 2018/0015264 A1 | 1/2018 | Wang et al. | |
| 2018/0296806 A1 | 10/2018 | Haery | |
| 2019/0038881 A1 | 2/2019 | Wang et al. | |
| 2019/0076283 A1 * | 3/2019 | Okumura | A61B 18/082 |
| 2019/0269493 A1 | 9/2019 | Okumura et al. | |
| 2019/0269494 A1 | 9/2019 | Okumura et al. | |

FOREIGN PATENT DOCUMENTS

| | | |
|---|---|---|
| JP | 2000-509304 A | 7/2000 |
| JP | 2002-538932 A | 11/2002 |
| JP | 2002-540838 A | 12/2002 |
| JP | 2003-507096 A | 2/2003 |
| JP | 2003-526460 A | 9/2003 |
| JP | 2004-000601 A | 1/2004 |
| JP | 2005-521476 A | 7/2005 |
| JP | 2007-508053 A | 4/2007 |
| JP | 2008-526461 A | 7/2008 |
| JP | 2009-533150 A | 9/2009 |
| JP | 2009-536083 A | 10/2009 |
| JP | 2010-533036 A | 10/2010 |
| JP | 2014-508580 A | 4/2014 |
| JP | 2014-521390 A | 8/2014 |
| JP | 2014-171629 A | 9/2014 |
| JP | 2014-188205 A | 10/2014 |
| JP | 2015-023904 A | 2/2015 |
| JP | 2015-033634 A | 2/2015 |
| JP | 2015-066144 A | 4/2015 |
| JP | 2016-032523 A | 3/2016 |
| JP | 2016-154927 A | 9/2016 |
| JP | 2016-185296 A | 10/2016 |
| JP | 2017-533036 A | 11/2017 |
| JP | 2018-504209 A | 2/2018 |
| WO | 1997/40877 A1 | 11/1997 |
| WO | 2000/56237 A2 | 9/2000 |
| WO | 00/59398 A1 | 10/2000 |
| WO | 2001/012255 A1 | 2/2001 |
| WO | 01/68015 A1 | 9/2001 |
| WO | 03/082359 A1 | 10/2003 |
| WO | 2005/037152 A1 | 4/2005 |
| WO | 2006/078672 A1 | 7/2006 |
| WO | 2007/120727 A1 | 10/2007 |
| WO | 2007/131112 A2 | 11/2007 |
| WO | 2009/009274 A2 | 1/2009 |
| WO | 2012/054387 A2 | 4/2012 |
| WO | 2012/099974 A2 | 7/2012 |
| WO | 2012/162114 A1 | 11/2012 |
| WO | 2015/016162 A1 | 2/2015 |
| WO | 2016/070032 A1 | 5/2016 |
| WO | 2016/118923 A1 | 7/2016 |
| WO | 2016/158290 A1 | 10/2016 |
| WO | 019/193738 A1 | 10/2019 |

* cited by examiner

GASTROINTESTINAL TRACT CONSTRICTING METHOD

TECHNICAL FIELD

The present invention relates to a gastrointestinal-tract constricting method.

BACKGROUND ART

Heretofore, known methods for treating gastroesophageal reflux disease, which is a benign disorder caused by degradation of the function of the cardiac sphincter at the entrance of the stomach, include oral administration of a proton pump inhibitor (PPI) that decreases the amount of gastric acid, the Nissen fundoplication technique (fundoplication technique) that involves wrapping a part of the stomach around the esophagus, the LINX technique that involves squeezing the esophagus with a magnet band or rubber band, the transoral incisionless fundoplication (TIF) technique that involves pulling the cardiac part under peroral endoscopy and stapling the cardiac part in the pulled state to form a valve, etc.

In addition, the methods described in, for example, PTL 1 and PTL 2 are other known methods for treating gastroesophageal reflux disease. The method described in PTL 1 involves removing tissue from a surface of the gastrointestinal tract, such as the esophagus, the stomach, or the like, and re-constructing the body passageway by utilizing the healing response. In PTL 2, the gastrointestinal tract is constricted by deliberately causing scars to form by incising at least one of the mucosal layer and the submucosal layer in the gastroesophageal junction or stomach.

CITATION LIST

Patent Literature

{PTL 1} Japanese Translation of PCT International Application, Publication No. 2009-536083
{PTL 2} US Patent Application No. 2015/0374352

SUMMARY OF INVENTION

An aspect of the present invention provides a gastrointestinal-tract constricting method that comprises: while observing the gastrointestinal tract with an endoscope inserted into the gastrointestinal tract, placing a protection substance, which does not damage tissue, in at least one of a region between the mucosal layer and muscular layer of the gastrointestinal tract and a region in a mucosal surface of the mucosal layer so as to form a protection region that protects the mucosa basal layer from a medical substance that damages the tissue; and after forming the protection region, supplying the medical substance to a mucosal surface in a target region, which is at a position different from the protection region in the circumferential direction of the gastrointestinal tract, or to a position between the mucosal layer and the muscular layer in the target region.

DESCRIPTION OF EMBODIMENTS

First Embodiment

A gastrointestinal-tract constricting method according to a first embodiment of the present invention will now be described with reference to the drawings.

Figure 1:
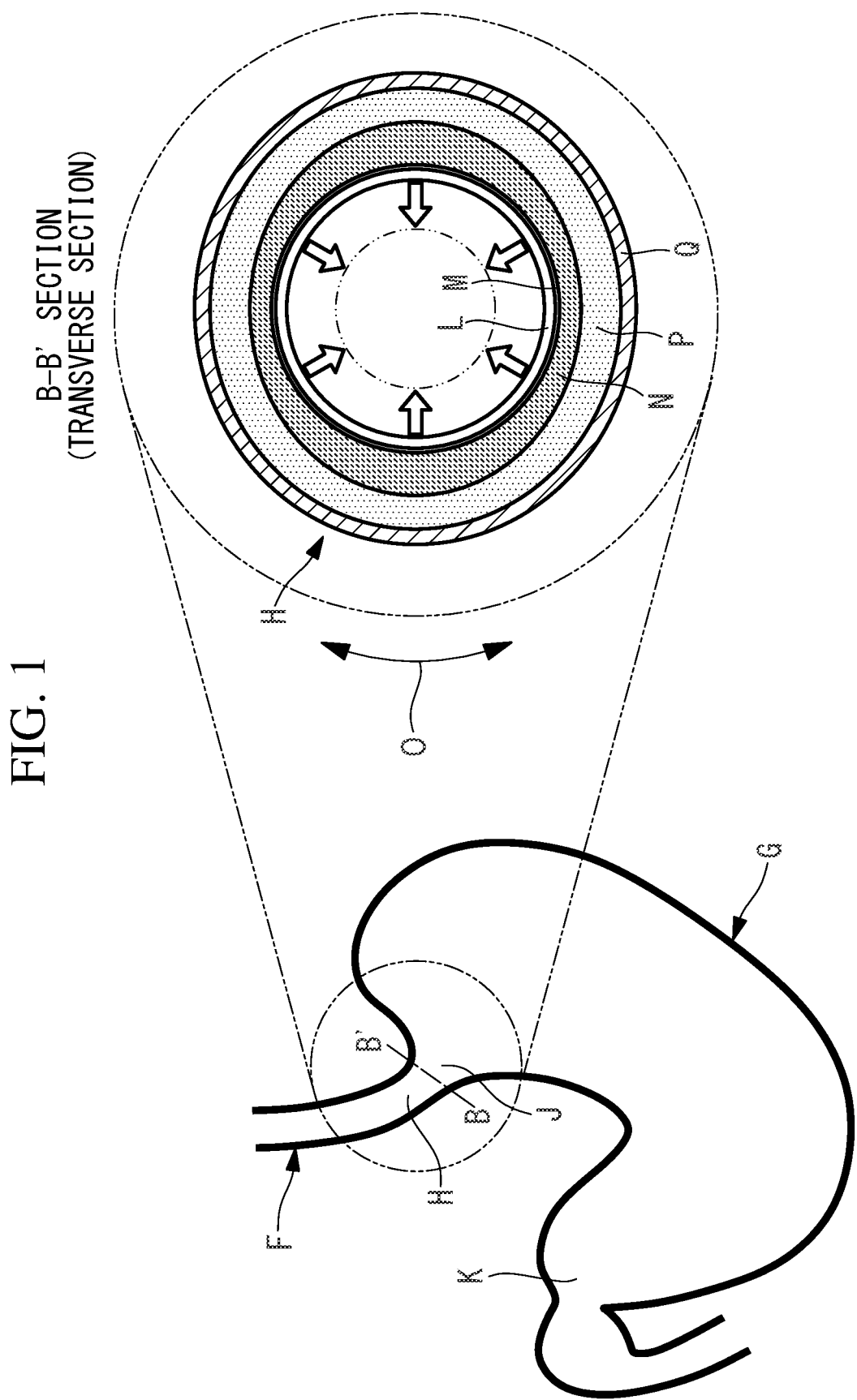
FIG. 1 includes a diagram illustrating a periphery of the gastroesophageal junction to which a gastrointestinal-tract constricting method according to a first embodiment of the present invention is applied, and a cross-sectional view taken at B-B' illustrating a transverse section of the gastroesophageal junction.

The case described as an example in this embodiment is the case in which the gastrointestinal-tract constricting method is applied to the treatment of gastroesophageal reflux disease, wherein, as illustrated in FIG. 1, a part of a region that extends from the gastroesophageal junction (lower part of the esophagus) H, where the esophagus F connects to the stomach G, to the cardiac part is constricted. In FIG. 1, reference sign J denotes the cardiac part constituting the entrance of the stomach G, reference sign K denotes the pyloric part constituting the endmost part of the stomach G, reference sign L denotes the mucosal layer, reference sign N denotes the mucosa basal layer, reference sign N denotes the submucosal layer, reference sign P denotes the muscular layer, and reference sign Q denotes the serosa.

Figure 2:
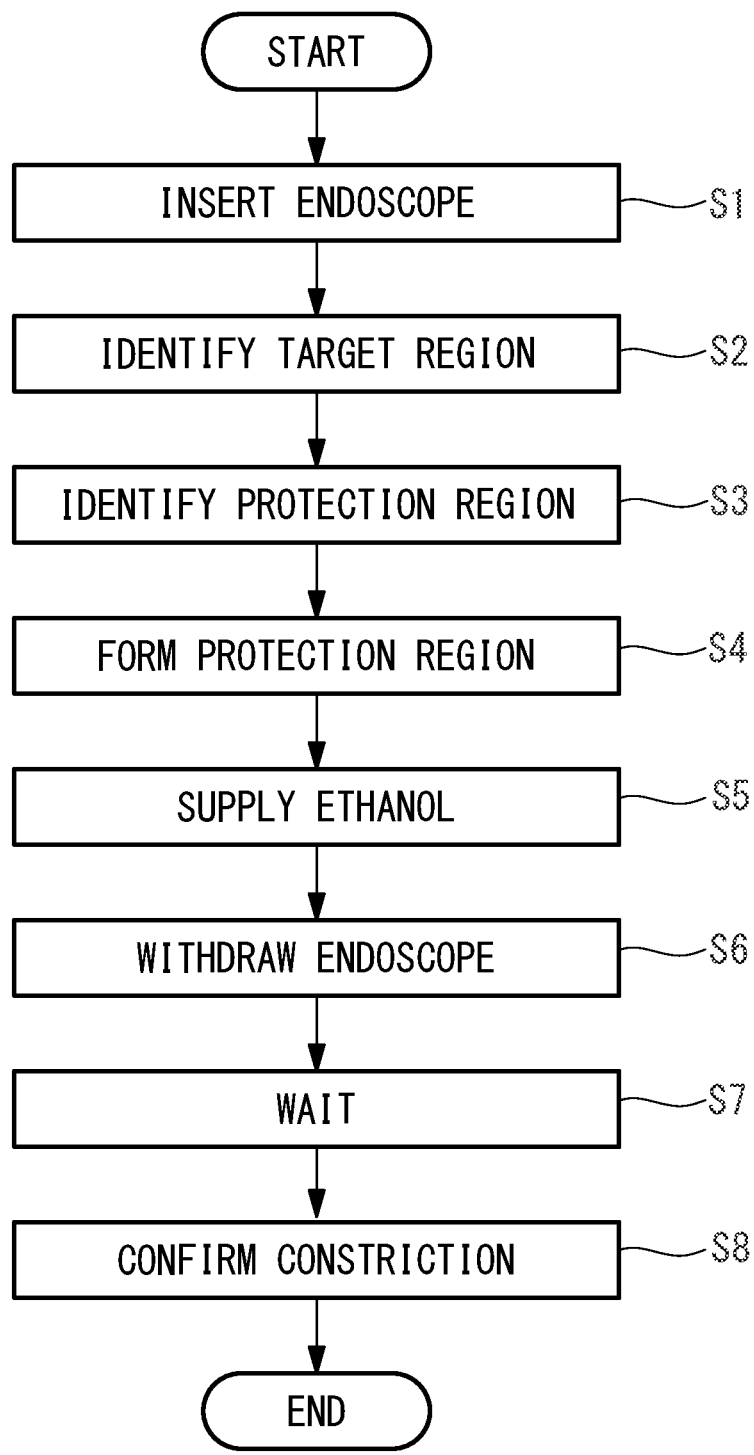
FIG. 2 is a flowchart illustrating the gastrointestinal-tract constricting method according to the first embodiment of the present invention.

As illustrated in the flowchart of FIG. 2, the gastrointestinal-tract constricting method includes an inserting step S1 of inserting an endoscope into the gastrointestinal tract constituting the gastroesophageal junction H; a first identifying step S2 of identifying a target region where the mucosa basal layer M of the gastroesophageal junction H is to be damaged by ethanol (medical substance) while observing the gastroesophageal junction H with an endoscope; a second identifying step S3 of identifying a protection region where the mucosa basal layer M is to be protected from ethanol, the protection region being at a position different from the target region in the circumferential direction of the gastrointestinal tract; a forming step S4 of forming the protection region; a supplying step S5 of supplying ethanol to the target region after the forming step S4; an endoscope withdrawing step S6 of withdrawing an endoscope 1 from the inside of the gastrointestinal tract to the outside of the body; a waiting step S7 of waiting until a part of the region extending from the gastroesophageal junction H to the cardiac part J is constricted; and a constriction confirming step S8 of confirming constriction of the part of the region extending from the gastroesophageal junction H to the cardiac part J.

Figure 3:
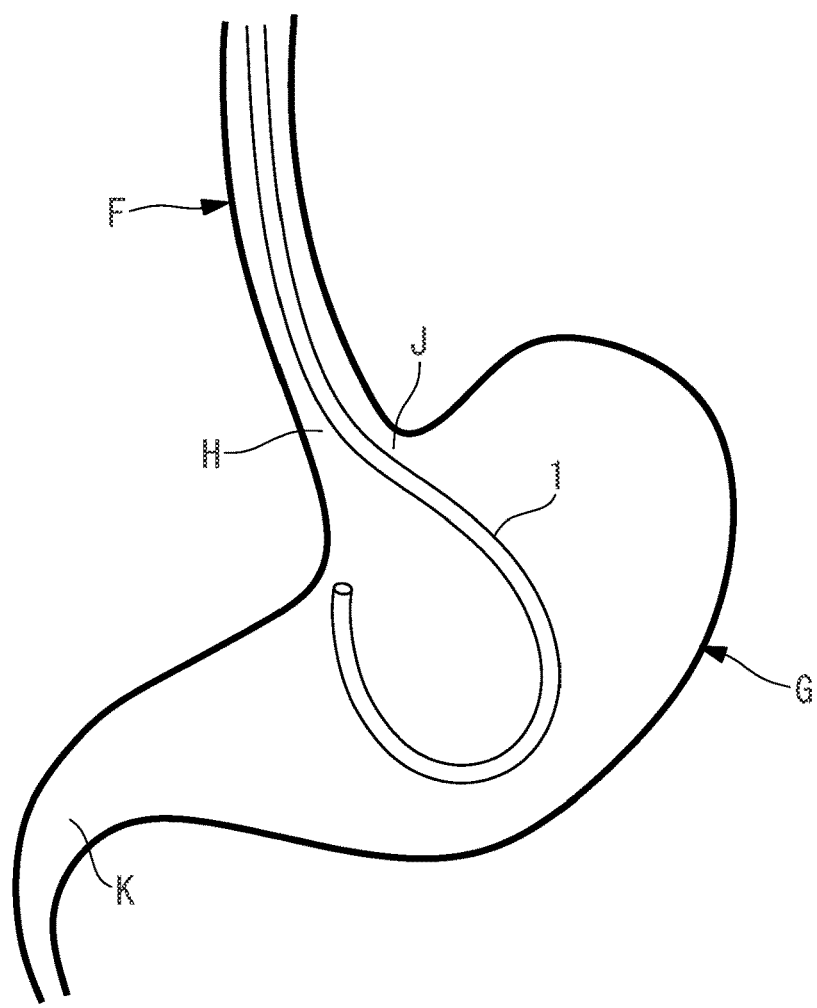
FIG. 3 is a diagram showing how an endoscope is inserted into the stomach illustrated in FIG. 1.

As illustrated in FIG. 3, in the inserting step S1, the endoscope 1 is inserted via the mouth of a subject into the stomach G through the esophagus F, the distal end of the endoscope 1 is bent inside the stomach G, and the distal end of the endoscope 1 is arranged to face the cardiac part J and the gastroesophageal junction H as if to look up into the esophagus F from the stomach G.

Figure 4:
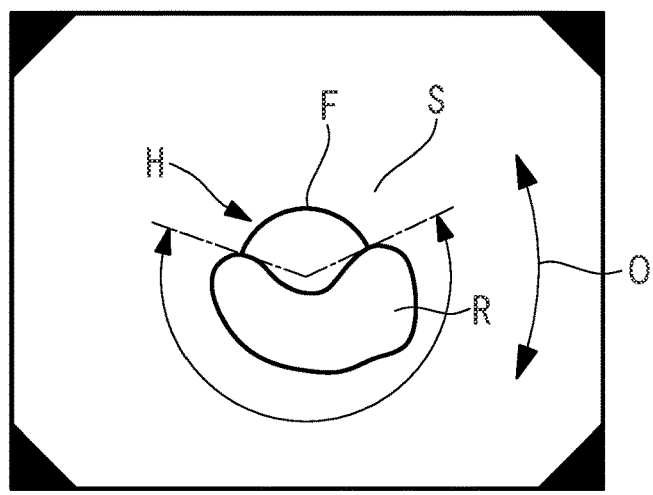
FIG. 4 is an endoscopic image of the gastroesophageal junction illustrated in FIG. 1 and a mucosal surface in a target region, as viewed from the inside of the stomach.

As illustrated in FIG. 4, in the first identifying step S2, after the mucosal surface of the relaxed cardiac part J is observed with the endoscope 1, the range of a target region R on the surface of the mucosal layer L is identified. In the drawing, reference sign S denotes the gastric wall, and the arrow indicated by reference sign O indicates the circumferential direction of the gastrointestinal tract.

In the supplying step S5 described below, in the range coincident with the identified target region R, the mucosa basal layer M (refer to FIG. 1), which is the lowermost layer of the mucosal layer L, in a part of the region extending from the gastroesophageal junction H to the cardiac part J is damaged. By damaging the mucosa basal layer M in the target region R, constriction occurs in part of the region extending from the gastroesophageal junction H to the cardiac part J. Preferably, the range of the target region R is appropriately determined in advance so that the lumen has a desired inner diameter after constriction.

In order to prevent excessive constriction, the target region R is set to be a part of the region extending from the gastroesophageal junction H to the cardiac part J, and is a range that does not extend all around the circumference. For example, as illustrated in FIG. 4, the target region R is preferably a range that extends from the lesser curvature side to the gastric fundus side and occupies 60% to 80% of the entire circumference.

Figure 5:
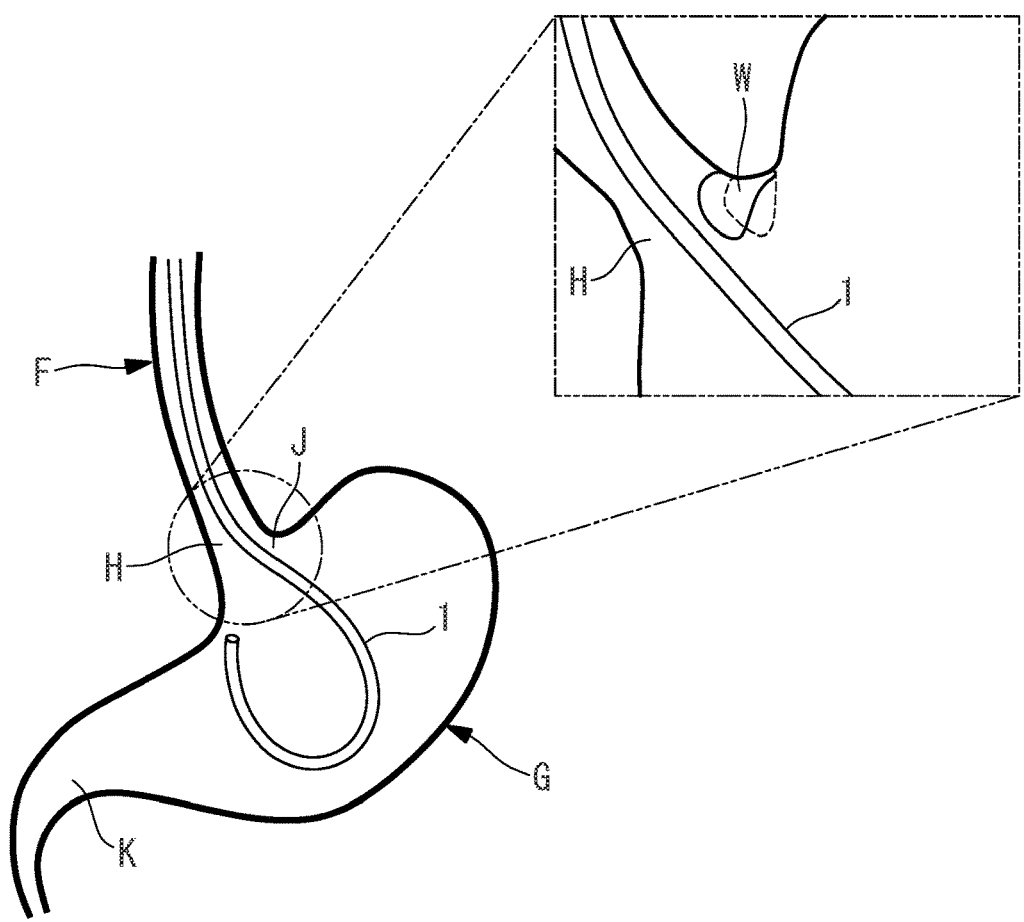
FIG. 5 is a diagram illustrating the position where a protection region is formed in the gastroesophageal junction.
Figure 6:
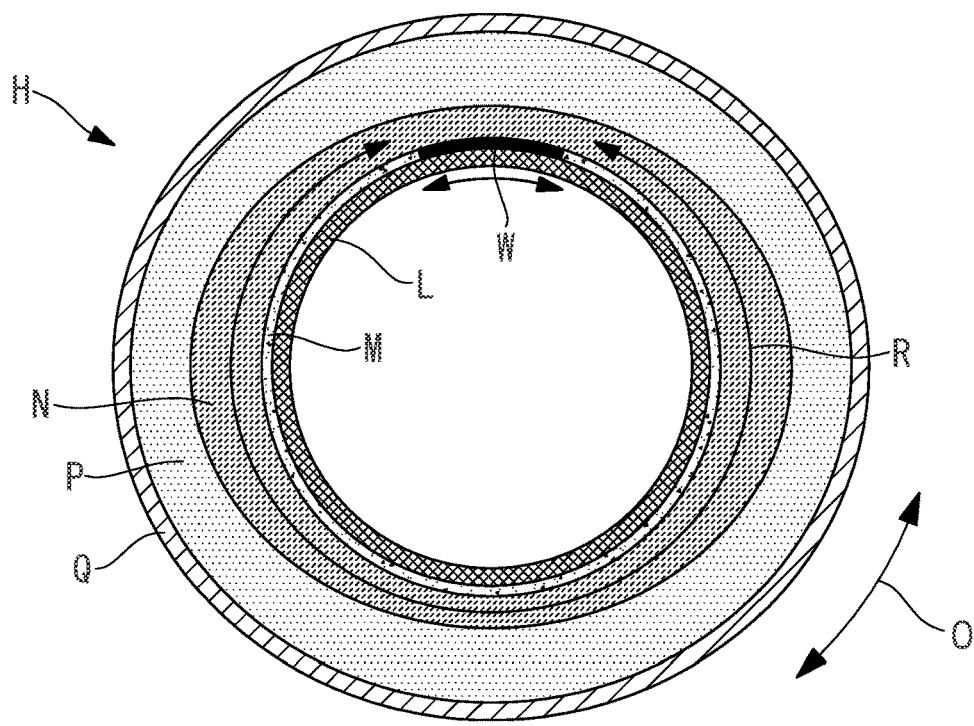
FIG. 6 is a cross-sectional view of the gastroesophageal junction taken along B-B' in FIG. 1 and illustrates the position where the protection region is to be formed.

As illustrated in FIGS. 5 and 6, in the second identifying step S3, while the relaxed gastroesophageal junction H is observed with the endoscope 1, the range of a protection region W on the surface of the mucosal layer L is identified. The position at which the range of the protection region W is identified is a position different from the target region R in the circumferential direction of the gastrointestinal tract, in other words, the position that is not in the target region R identified by the first identifying step S2. Specifically, the position at which the range of the protection region W is identified is preferably a position on the side remote from the pyloric part K in the circumferential direction of the gastrointestinal tract.

In the forming step S4, a protection substance is supplied to the submucosal layer (position between the mucosal layer L and the muscular layer P) N in the gastroesophageal junction H so as to form the protection region W in the region between the mucosal layer L and the muscular layer P. An example of the protection substance used is a sodium hyaluronate solution, which does not damage the tissue (in particular, the mucosa basal layer M). Sodium hyaluronate is immiscible with ethanol due to its chemical polarity. Moreover, since sodium hyaluronate has a higher viscosity than ethanol, sodium hyaluronate does not easily spread around and is likely to stay at the site between the mucosal layer L and the muscular layer P. The chemical polarity referred to here is the electrical bias present within the molecule.

Figure 7:
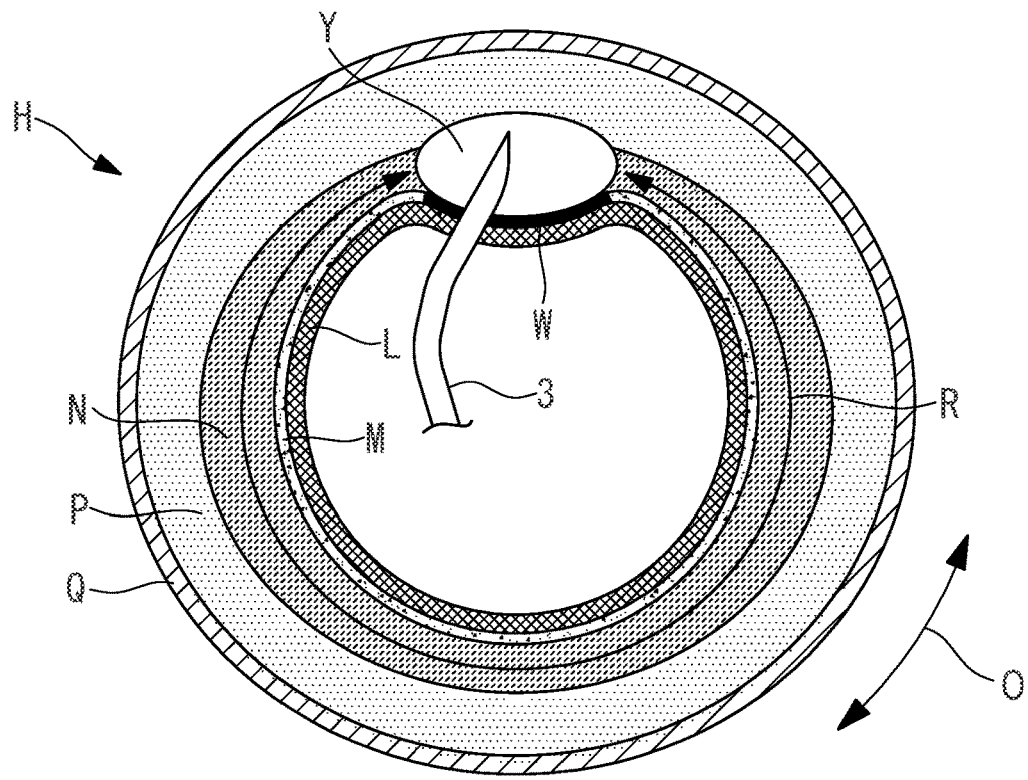
FIG. 7 is a cross-sectional view of the gastroesophageal junction taken along B-B' in FIG. 1 and illustrates how the protection region is formed by injecting a sodium hyaluronate solution into the submucosal layer.

As illustrated in FIG. 7, in the forming step S4, an injection needle 3 of an injection-needle-equipped treatment tool is used to inject a sodium hyaluronate solution Y at a position between the mucosal layer L and the muscular layer P and within the protection region W identified in the second identifying step S3 so as to form the protection region W in the region between the mucosal layer L and the muscular layer P. The protection region W protects the mucosa basal layer N adjacent to the protection region W, which is filled with the sodium hyaluronate solution Y, in the radial direction of the gastrointestinal tract. The sodium hyaluronate solution Y can remain at the injected position in the submucosal layer N due to its high viscosity.

Figure 8:
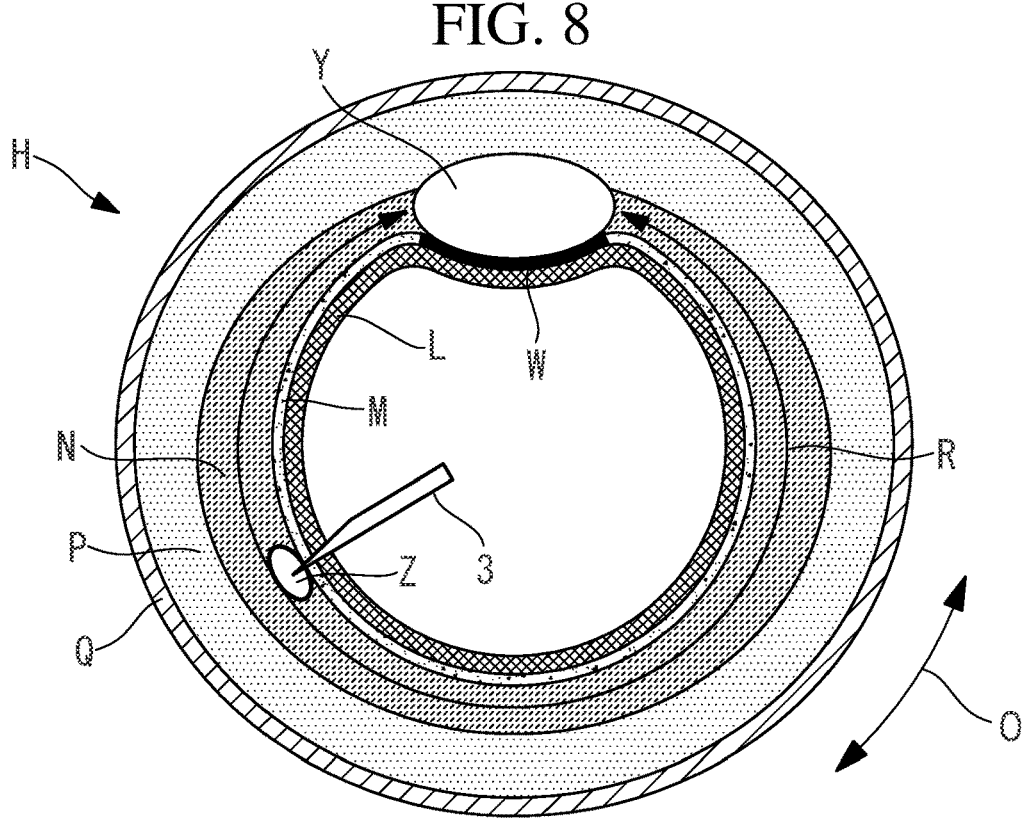
FIG. 8 is a cross-sectional view of the gastroesophageal junction taken along B-B' in FIG. 1, and illustrates how ethanol is injected into the target region.
Figure 9:
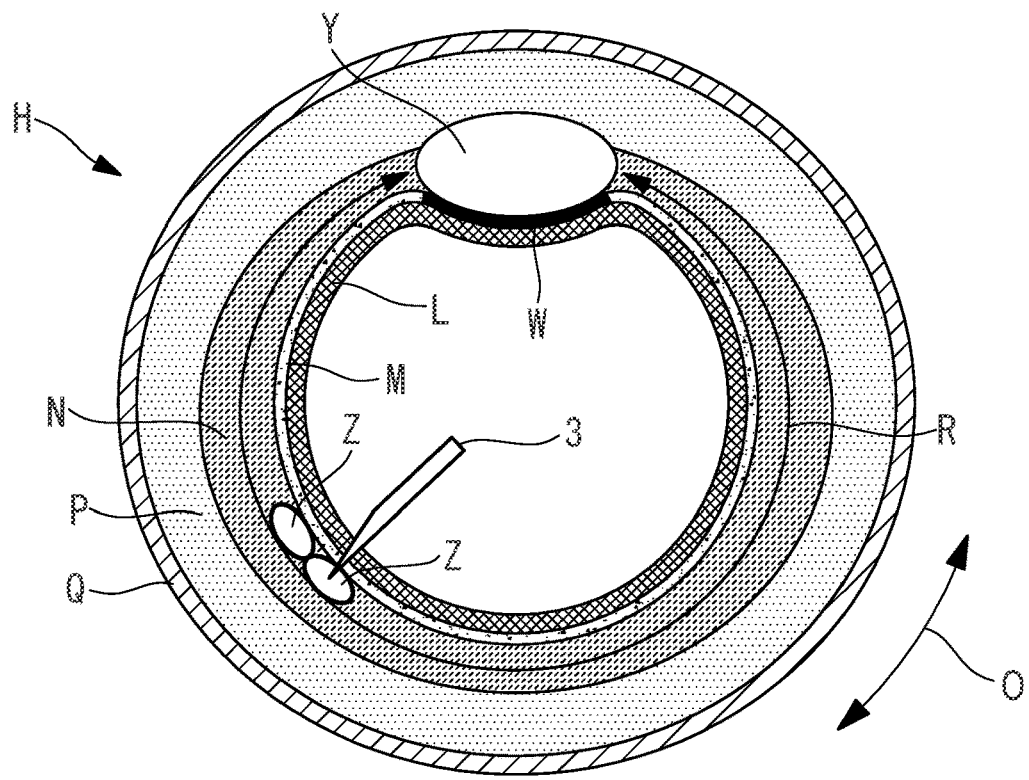
FIG. 9 is a cross-sectional view of the gastroesophageal junction taken along B-B' in FIG. 1, and illustrates how ethanol is injected while shifting the position within the target region.
Figure 10:
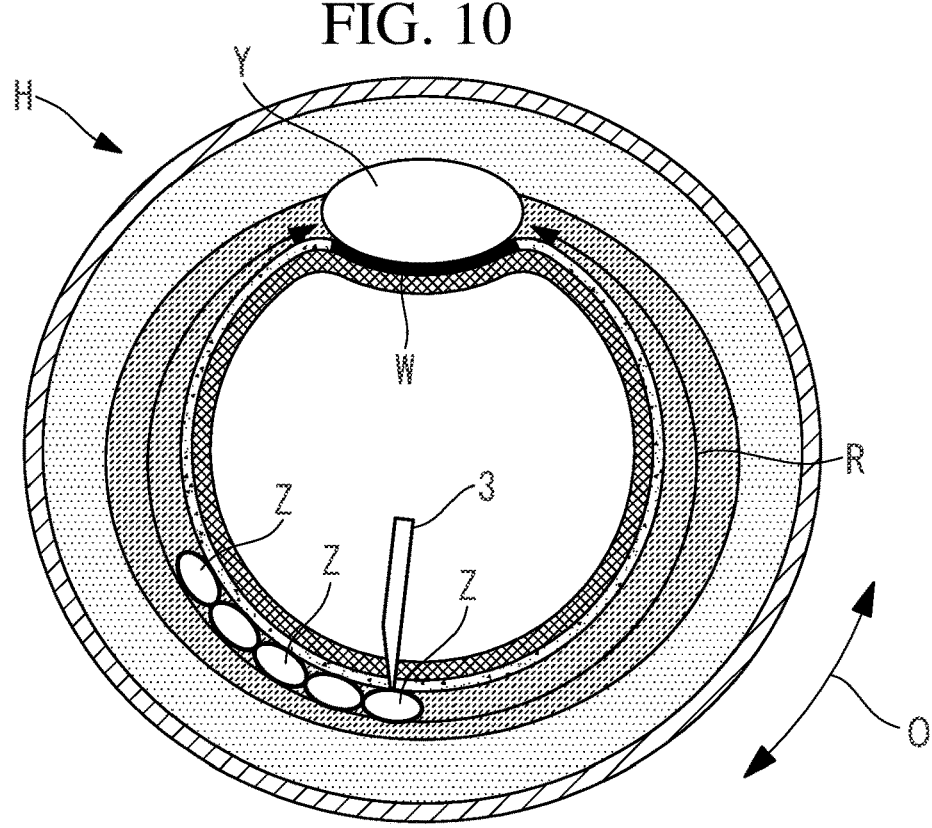
FIG. 10 is a cross-sectional view of the gastroesophageal junction taken along B-B' in FIG. 1, and illustrates how ethanol is injected while further shifting the position within the target region.

In the supplying step S5, as illustrated in FIGS. 8, 9, and 10, the operation of injecting ethanol Z into the submucosal layer (the position between the mucosal layer L and the muscular layer P) N in the target region R by using the injection needle 3 of the injection-needle-equipped treatment tool is repeated several times while shifting the position within the target region R.

The effects of the gastrointestinal-tract constricting method according to this embodiment will now be described.

In order to constrict a part of the region extending from the gastroesophageal junction H to the cardiac part J of the subject by the gastrointestinal-tract constricting method of this embodiment, first, as illustrated in FIG. 3, the endoscope 1 is inserted into the gastrointestinal tract through the mouth of the subject, and the distal end of the endoscope 1 is bent inside the stomach G so as to face the cardiac part J and the gastroesophageal junction H (inserting step S1).

Next, as illustrated in FIGS. 4, 5, and 6, while observing the region that extends from the gastroesophageal junction H to the cardiac part J with the endoscope 1, the target region R is identified within the region that extends from the gastroesophageal junction H to the cardiac part J (first identifying step S2), and, the protection region W is identified at a position different from the identified target region R in the circumferential direction of the gastrointestinal tract (second identifying step S3). The order in which the first identifying step and the second identifying step are performed may be reversed.

Once the target region R and the protection region W are identified, the injection-needle-equipped treatment tool is inserted into a forceps channel of the endoscope 1, and a syringe (not illustrated) filled with the sodium hyaluronate solution Y is attached to the injection-needle-equipped treatment tool.

Then, as illustrated in FIG. 7, the injection needle 3 of the injection-needle-equipped treatment tool punctures the identified protection region W, and the sodium hyaluronate solution Y is injected into the submucosal layer N so as to form the protection region W. The protection region W protects the mucosa basal layer M adjacent to the protection region W, which is filled with the sodium hyaluronate solution Y, in the radial direction of the gastrointestinal tract (forming step S4). Preferably, the protection region W is formed along the longitudinal axis of the gastroesophageal junction. The protection region W may have, for example, a shape such that at least part of the transverse section thereof extends in an arc shape along the circumferential direction of the gastrointestinal tract.

After the protection region W is formed, a syringe (not illustrated) filled with ethanol is attached to the injection-needle-equipped treatment tool so as to replace the syringe which has been filled with the sodium hyaluronate solution Y. Next, as illustrated in FIG. 8, the target region R is punctured with the injection needle 3 of the injection-needle-equipped treatment tool so as to inject the ethanol Z into the submucosal layer N. Then, as illustrated in FIGS. 9 and 10, this operation is repeated several times while shifting the position in the circumferential direction of the gastrointestinal tract within the range of the target region R (supplying step S5).

Figure 11:
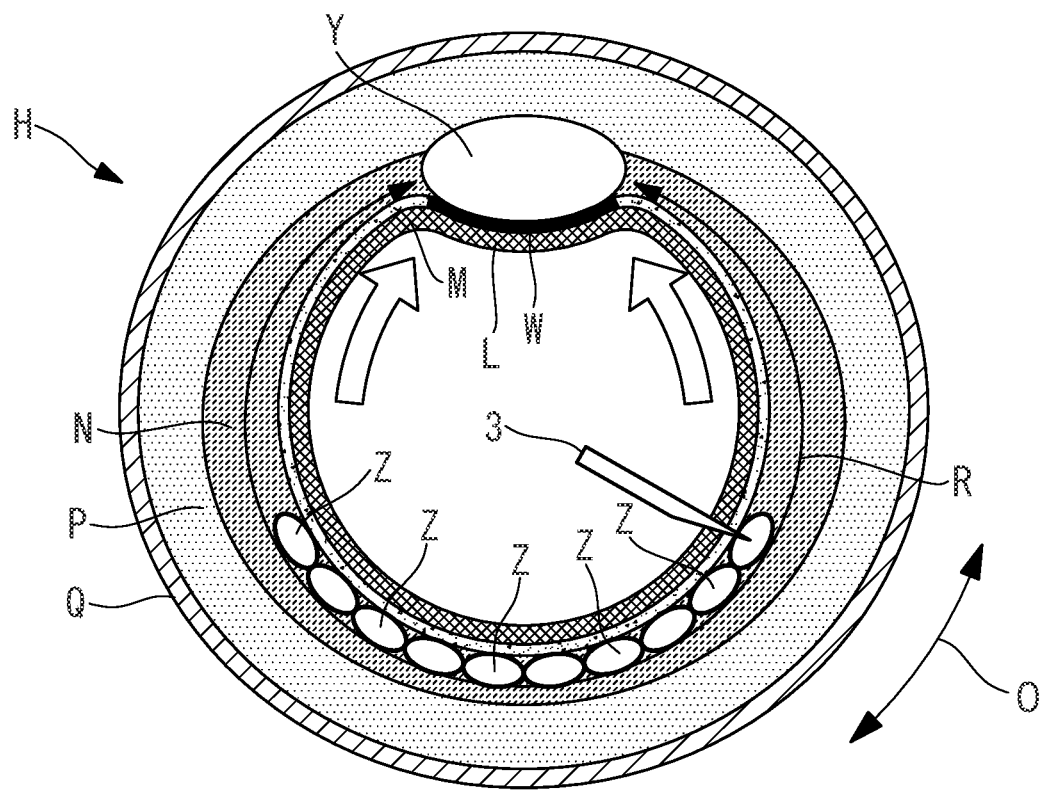
FIG. 11 is a cross-sectional view of the gastroesophageal junction taken along B-B' in FIG. 1, and illustrates how ethanol injected into the target region spreads in the circumferential direction of the gastroesophageal junction.

In the supplying step S5, as illustrated in FIG. 11, the ethanol Z injected into the submucosal layer N in the target region R spreads within the submucosal layer N. The ethanol Z is repeatedly injected into the submucosal layer N while shifting the position within the range of the target region R until the ethanol Z that has spread within the submucosal layer N reaches and contacts the sodium hyaluronate solution Y in the protection region W.

As a result, the mucosa basal layer M in the target region R is damaged by the ethanol Z. When the ethanol Z is injected into the submucosal layer N, the surface of the mucosal layer L located above that submucosal layer N bulges. Thus, the range in which the ethanol Z injected into the submucosal layer N has spread can be confirmed by the position of the bulge on the surface of the mucosal layer L. Whether the ethanol has reached and contacted the sodium hyaluronate solution Y injected into the submucosal layer N in the protection region W can also be confirmed by the position of the bulge on the surface of the mucosal layer L.

After the supplying step S5, the endoscope 1 is withdrawn out of the body from the gastrointestinal tract (endoscope withdrawing step S6). After the endoscope 1 is withdrawn out of the body from the gastrointestinal tract, the operation thereof is waited until the part of the region extending from the gastroesophageal junction H to the cardiac part J is constricted by the constrictive effect of the tissue around the target region R undergoing the process of scar formation as the damaged tissue heals (waiting step S7).

After waiting of the operation until the part of the region extending from the gastroesophageal junction H to the cardiac part J is constricted, the endoscope 1 is again inserted into the gastrointestinal tract so as to confirm that the part of the region extending from the gastroesophageal junction H to the cardiac part J is constricted (constriction confirming step S8). The mucosa basal layer M is damaged by the ethanol Z within the range of the desired target region R set to be a part of the region extending from the gastroesophageal junction H to the cardiac part J and set not to extend all around the circumference. In this manner, since a part of the region extending from the gastroesophageal junction H to the cardiac part J can be constricted, reflux of the gastric acid can be suppressed without excessively constricting the part of the region that extends from the gastroesophageal junction H to the cardiac part J.

If needed, as described in the forming step S4, the sodium hyaluronate solution Y may be further injected into the submucosal layer N in the protection region W, and then as described in the supplying step S5, the ethanol Z may be further injected into the submucosal layer N in the target region R.

As described above, according to the gastrointestinal-tract constricting method of this embodiment, because the mucosa basal layer M in the target region R in the gastroesophageal junction H is damaged by the ethanol Z, the invasiveness is low and the procedure is easy compared to the case in which the mucosa basal layer M is damaged by excising the tissue in the gastroesophageal junction H.

In such a case, if the protection region W is not provided at a position different from the target region R in the circumferential direction of the gastrointestinal tract, the ethanol Z injected into the target region R will pass through the submucosal layer N and spread over the entire region in the circumferential direction of the gastrointestinal tract (the direction along the surface of the wall of the gastrointestinal tract). As a result, the ethanol Z damages the mucosa basal layer M all around the circumference of the gastrointestinal tract, and a part of the region extending from the gastroesophageal junction H to the cardiac part J may become excessively constricted.

Figure 12:
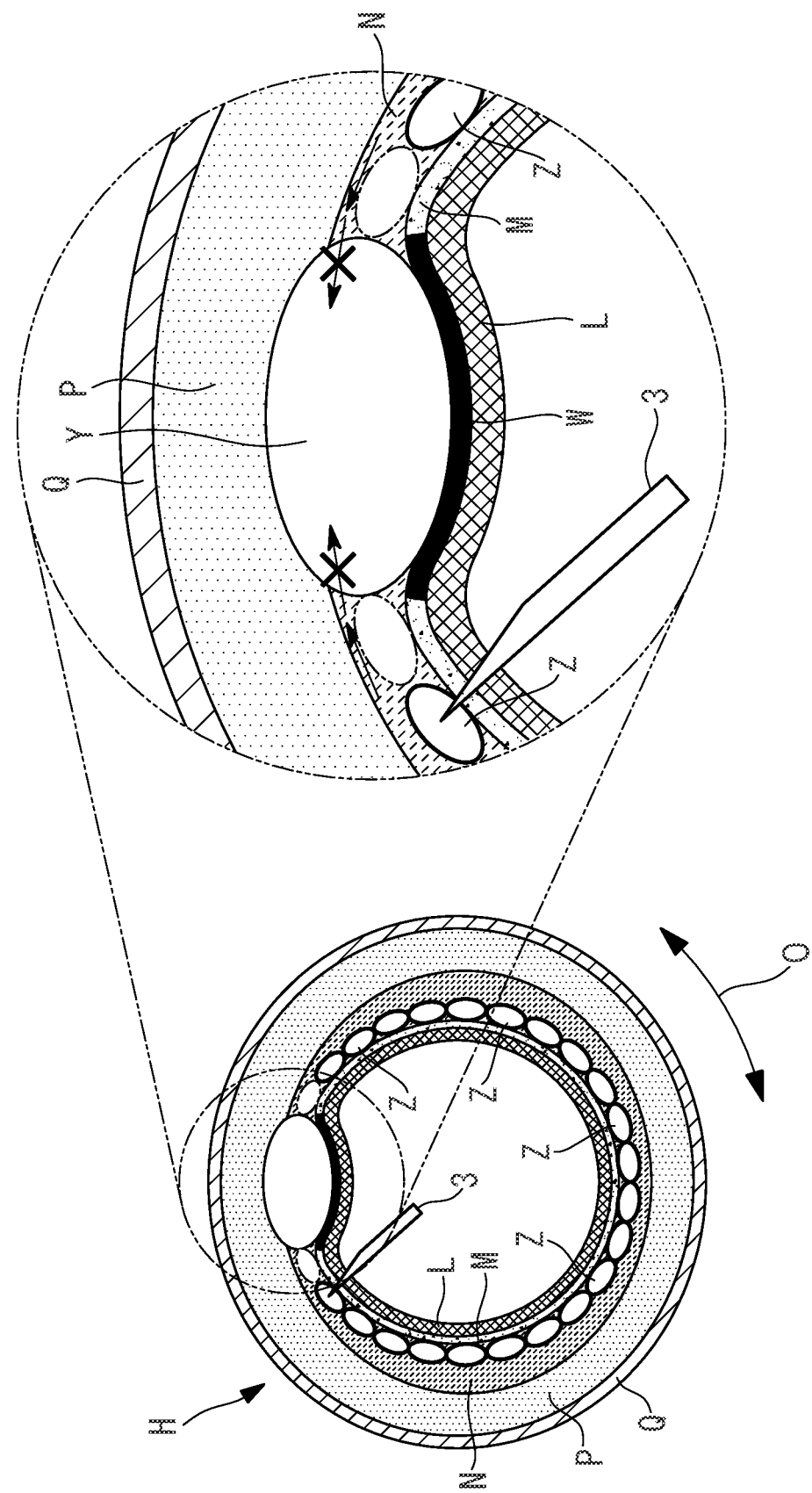
FIG. 12 is a cross-sectional view of the gastroesophageal junction taken along B-B' in FIG. 1, and illustrates how the sodium hyaluronate solution injected into the submucosal layer suppresses the penetration of ethanol into the submucosal layer in the protection region.

To address this issue, as illustrated in FIG. 11, before injecting ethanol Z into the target region R, the sodium hyaluronate solution Y is injected into the submucosal layer N at a position different from the target region R in the circumferential direction of the gastrointestinal tract so as to form the protection region W filled with the sodium hyaluronate solution Y. As a result, even if the ethanol Z injected into the target region R has passed through the submucosal layer N and spread in the circumferential direction of the gastrointestinal tract beyond what is necessary, penetration of the ethanol Z into the submucosal layer N in the protection region W can be suppressed, and damage to the mucosa basal layer M in the protection region W can be prevented, as illustrated in FIG. 12.

In this manner, damage to the mucosa basal layer M throughout the entire region in the circumferential direction of the gastrointestinal tract is prevented, and excessive constriction of a part of the region extending from the gastroesophageal junction H to the cardiac part J can be prevented. Thus, a part of the region that extends from the gastroesophageal junction H to the cardiac part J can be constricted by constricting the desired region of the gastroesophageal junction H by a simple and low-invasiveness procedure.

Second Embodiment

A gastrointestinal-tract constricting method according to a second embodiment of the present invention will now be described with reference to the drawings.

The gastrointestinal-tract constricting method according to this embodiment differs from the first embodiment in that, in the forming step S4, the protection substance is supplied to the surface of the mucosal layer L (mucosal surface) in the target region R, and, in the supplying step S5, the ethanol Z is supplied to the surface of the mucosal layer L. Other steps, S1 to S3 and S6 to S8, are the same as those in the first embodiment.

In the description of this embodiment, features common to the gastrointestinal-tract constricting method according to the first embodiment described above are denoted by the same reference signs, and descriptions therefor are omitted.

Figure 13:
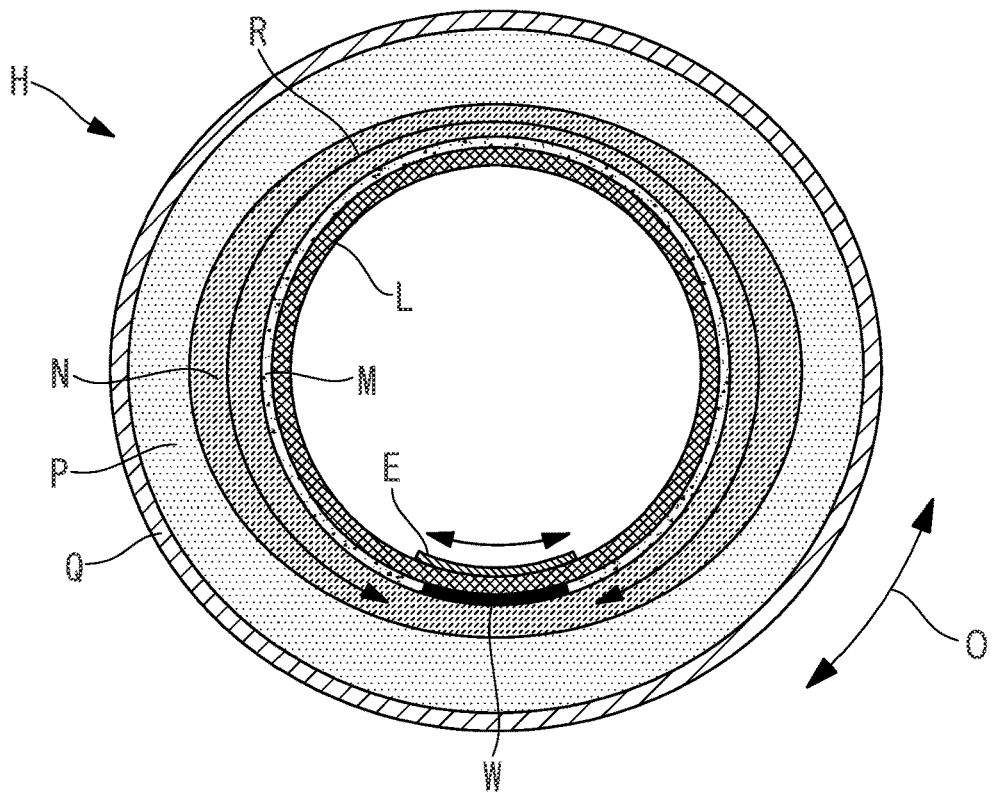
FIG. 13 is a cross-sectional view of the gastroesophageal junction taken along B-B' in FIG. 1, and illustrates how the protection region is formed by attaching a polylactate sheet onto a mucosal surface.

As illustrated in FIG. 13, in the forming step S4 of this embodiment, the surface of the mucosal layer L is coated by supplying a protection substance to the surface of the mucosal layer L in the protection region W identified in the second identifying step S3. As a result, the protection region W is formed in the mucosa basal layer M in a portion opposing the coated range in the radial direction of the gastrointestinal tract.

In this forming step S4, coating is preferably provided over a range larger than the identified protection region W on the surface of the mucosal layer L. In this manner, infiltration of the medical substance, which has been supplied to the surface of the mucosal layer L in the target region R and has circumvented the protection substance on the surface of the mucosal layer L, into the position between the mucosal layer L and the muscular layer P can be more effectively suppressed.

The protection substance is preferably a solid substance or a substance that does not damage the tissue of the mucosal layer L, and, in particular, that does not easily spread on the surface of the mucosal layer L due to its high viscosity. For example, a polylactate sheet is used as the protection substance. FIG. 13 illustrates how a polylactate sheet E is attached to the surface of the mucosal layer L.

Figure 14:
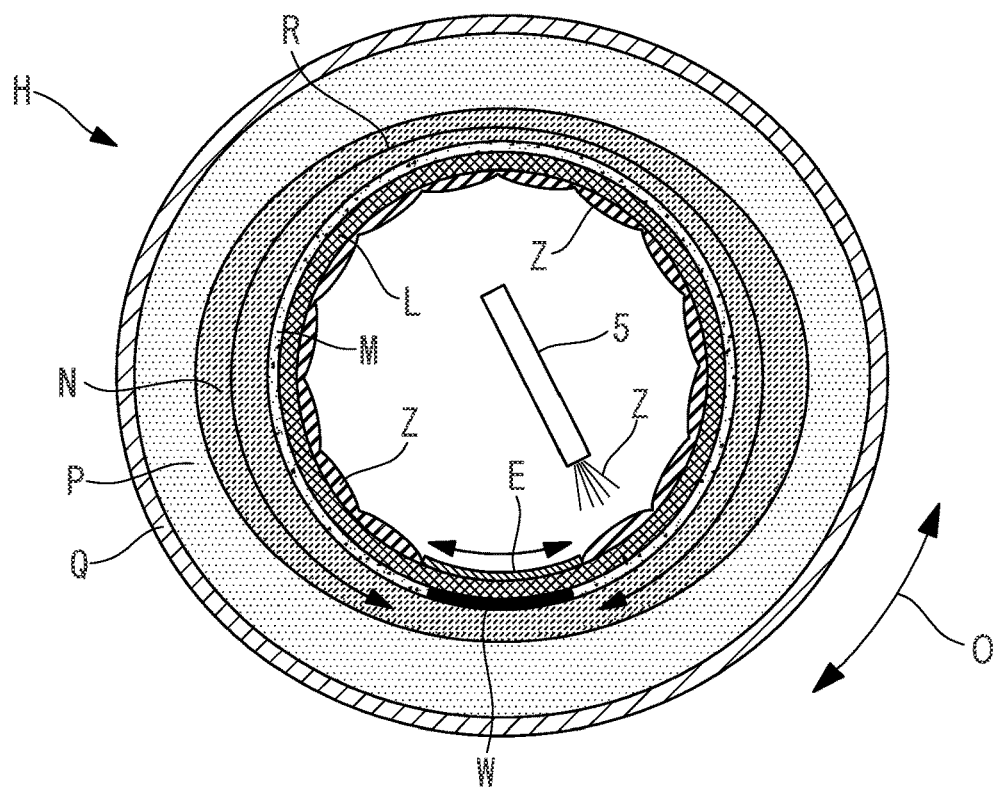
FIG. 14 is a cross-sectional view of the gastroesophageal junction taken along B-B' in FIG. 1, and illustrates how ethanol is sprayed onto the surface of the mucosal layer in the target region.

In the supplying step S5 according to this embodiment, as illustrated in FIG. 14, a spraying tube 5 is used to spray the ethanol Z onto the surface of the mucosal layer L in the target region R identified in the first identifying step S2.

According to the gastrointestinal-tract constricting method of this embodiment, before the ethanol Z is supplied to the target region R, the polylactate sheet E is attached to the surface of the mucosal layer L in the protection region W; thus, even when the ethanol Z penetrates the surface of the mucosal layer L in the protection region W, infiltration of the ethanol Z into the position between the mucosal layer L and the muscular layer P is blocked at the surface of the mucosal layer L, and damage to the mucosa basal layer M in the protection region W can be suppressed. In this manner, damage to the mucosa basal layer M all around the circumference of the gastrointestinal tract is prevented, and excessive constriction of a part of the region extending from the gastroesophageal junction H to the cardiac part J can be prevented.

Thus, according to the gastrointestinal-tract constricting method of this embodiment, a part of the region that extends from the gastroesophageal junction H to the cardiac part J can be constricted by constricting the desired region in the gastroesophageal junction H by a simple and low-invasiveness procedure that involves supplying the ethanol Z and the polylactate sheet E to the surface of the mucosal layer L in the gastroesophageal junction H.

Examples of the instance in which the ethanol Z penetrates the surface of the mucosal layer L in the protection region W include the instance in which, although the ethanol Z has been sprayed to avoid the protection region W, the ethanol Z has run over the surface of the mucosal layer L against the intention of the operator, and the instance in which the operator intentionally sprayed the ethanol Z all around the circumference of the gastrointestinal tract.

In this embodiment, the polylactate sheet E has been described as an example of the protection substance; alternatively, cyano acrylate may be employed as the protection substance. In such a case, cyano acrylate may be sprayed or applied onto the surface of the mucosal layer L in the protection region W. In the case where cyano acrylate is employed as the protection substance also, the protection region W can be formed by supplying the protection substance to the surface of the mucosal layer L by using a simple, low-invasiveness procedure, and infiltration of the ethanol Z into the position between the mucosal layer L and the muscular layer P in the protection region W can be blocked at the surface of the mucosal layer L.

Third Embodiment

A gastrointestinal-tract constricting method according to a third embodiment of the present invention will now be described with reference to the drawings.

Figure 15:
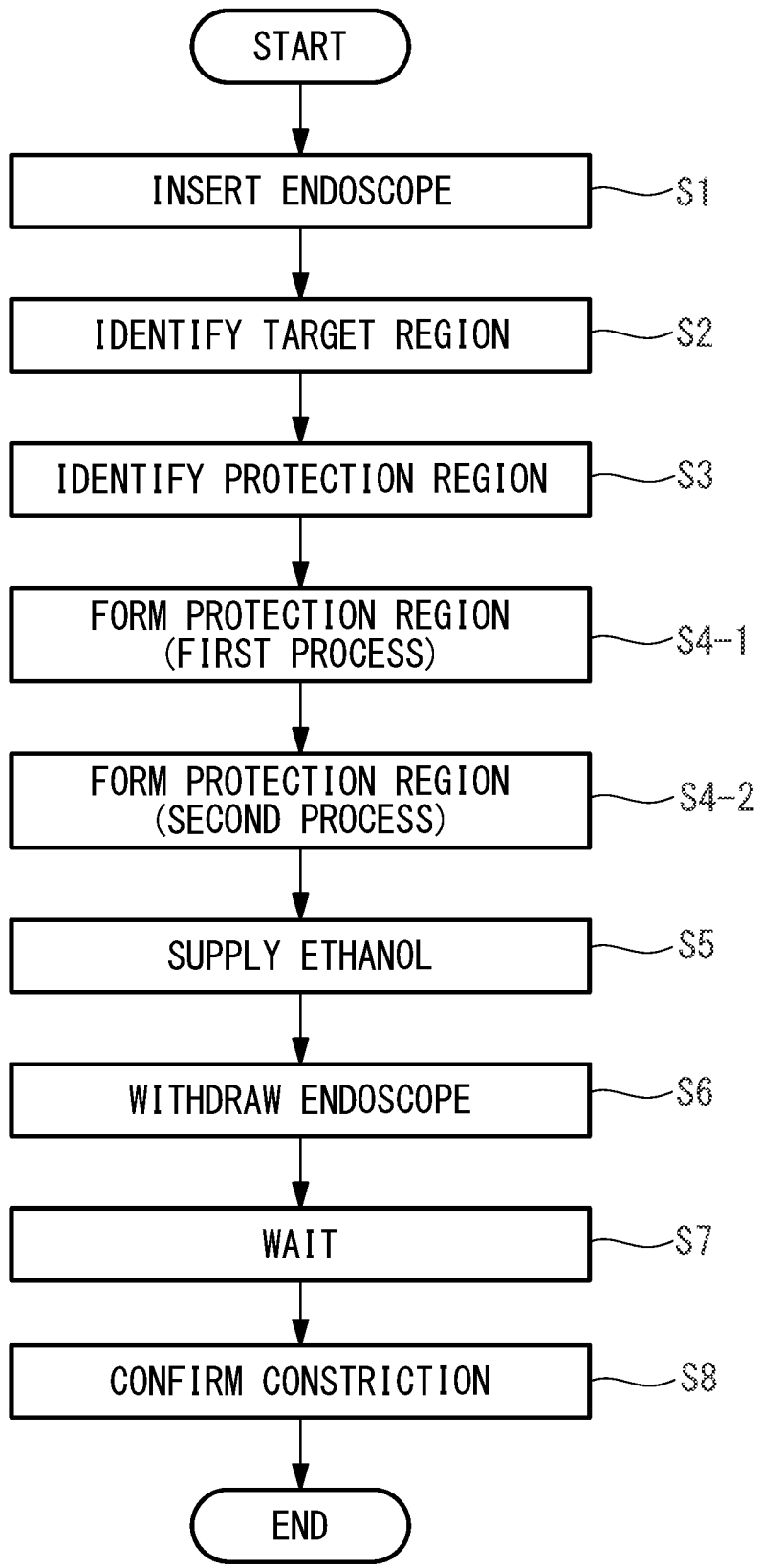
FIG. 15 is a flowchart illustrating the gastrointestinal-tract constricting method according to a third embodiment of the present invention.

As illustrated in the flowchart of FIG. 15, the gastrointestinal-tract constricting method of this embodiment differs from the second embodiment in that the method includes, instead of the forming step S4, a first forming step S4-1 of supplying the protection substance at a position between the mucosal layer L and the muscular layer P and different from the target region R in the circumferential direction of the gastrointestinal tract, and a second forming step S4-2 that supplies another protection substance to the surface of the mucosal layer L at the position where the protection substance is supplied. Other steps, S1 to S3 and S5 to S8, are the same as those of the second embodiment.

In the description of this embodiment, features common to the gastrointestinal-tract constricting methods according to the first and second embodiments described above are denoted by the same reference signs, and descriptions thereof are omitted.

Figure 16:
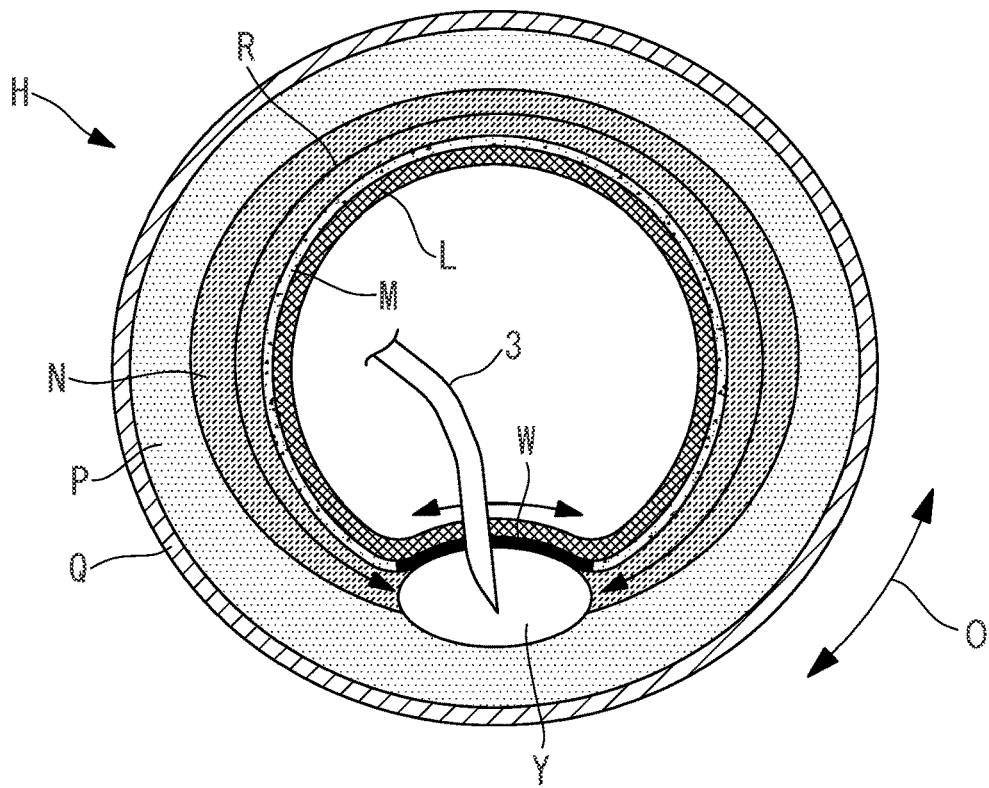
FIG. 16 is a cross-sectional view of the gastroesophageal junction taken along B-B' in FIG. 1, and illustrates how a sodium hyaluronate solution is injected into the submucosal layer in the identified protection region.

As illustrated in FIG. 16, in the first forming step S4-1, by using the injection needle 3 of the injection-needle-equipped treatment tool, the sodium hyaluronate solution (protection substance) Y is injected into the position between the mucosal layer L and the muscular layer P in the protection region W identified in the second identifying step S3.

Figure 17:
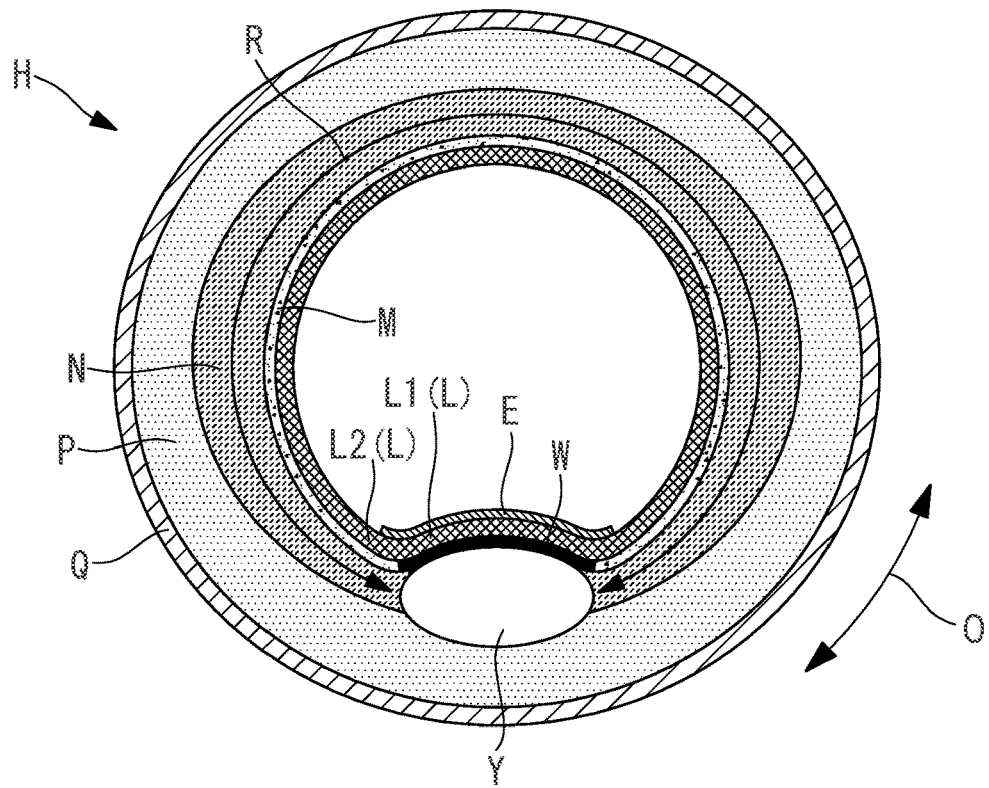
FIG. 17 is a cross-sectional view of the gastroesophageal junction taken along B-B' in FIG. 1, and illustrates how a polylactate sheet is attached onto a surface of the mucosal layer in the identified protection region.

As illustrated in FIG. 17, in the second forming step S4-2, the polylactate sheet (protection substance) E is attached to the surface of the mucosal layer L that has bulged by injection of the sodium hyaluronate solution Y into the position between the mucosal layer L and the muscular layer P in the first forming step S4-1 so as to coat the surface of the mucosal layer L. The polylactate sheet E preferably covers at least the boundary between a bulged portion L1, which the surface of the mucosal layer L is bulged due to the sodium hyaluronate solution Y, and a flat portion L2 that is not bulged.

Figure 18:
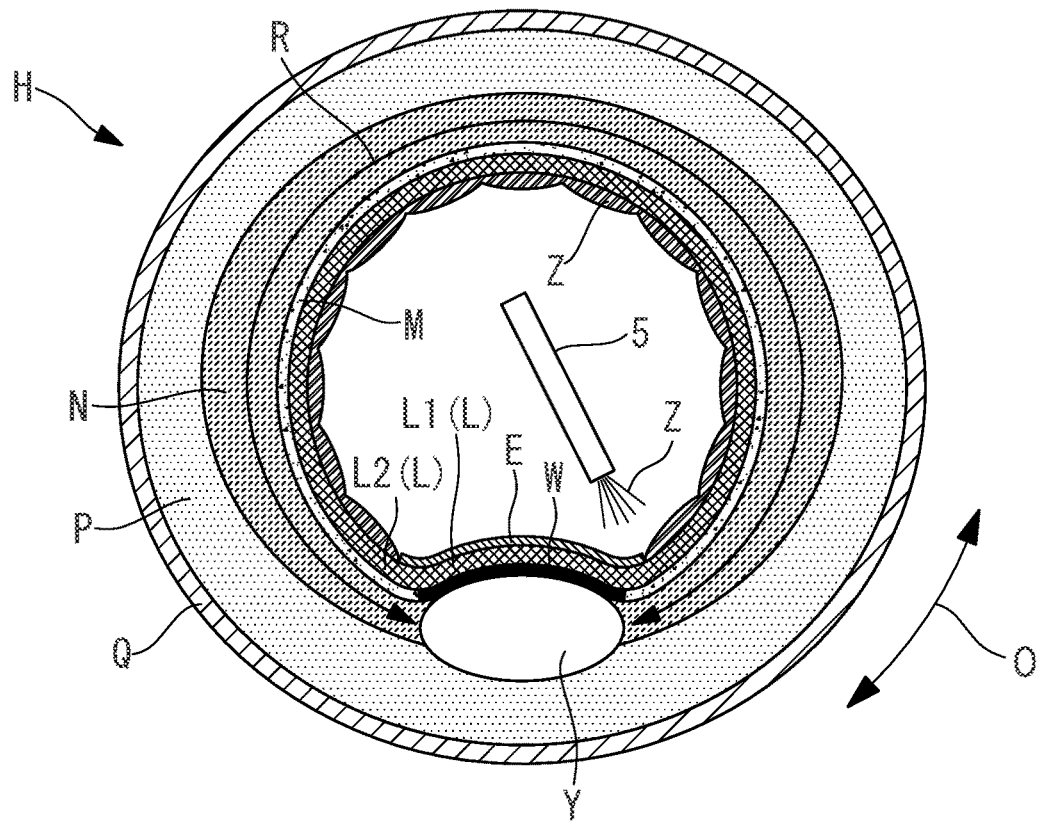
FIG. 18 is a cross-sectional view of the gastroesophageal junction taken along B-B' in FIG. 1, and illustrates how ethanol is sprayed onto the surface of the mucosal layer in the target region.

As illustrated in FIG. 18, in the supplying step S5 of this embodiment, the spraying tube 5 is used to spray the ethanol Z onto the surface of the mucosal layer L in the target region R identified in the first identifying step S2.

Figure 19:
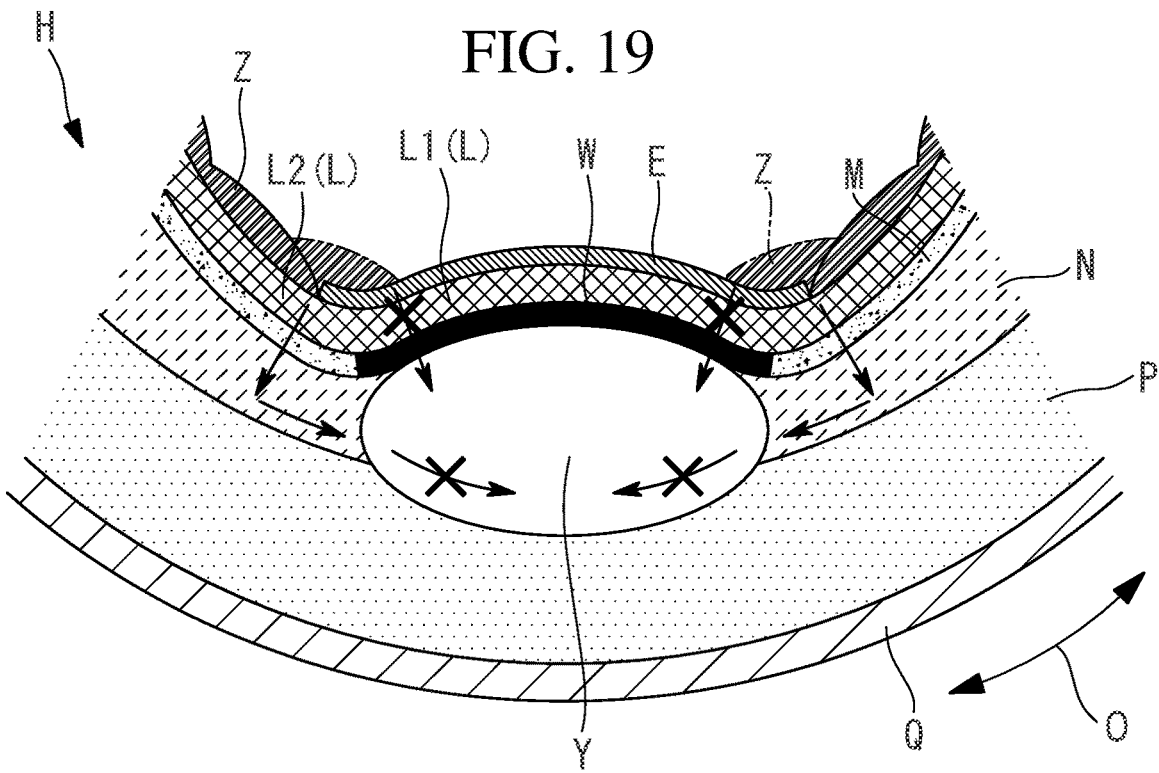
FIG. 19 is a partial enlarged view of a section of the gastroesophageal junction taken along B-B' in FIG. 1, and illustrates how the sodium hyaluronate solution injected into the submucosal layer and the polylactate sheet attached to the surface of the mucosal layer suppress the penetration of ethanol into the submucosal layer in the protection region.

As illustrated in FIG. 19, according to the gastrointestinal-tract constricting method of this embodiment, even if the sprayed ethanol Z has penetrated the surface of the mucosal layer L in the protection region W, the polylactate sheet E attached to the surface of the mucosal layer L in the protection region W blocks infiltration of the ethanol Z into the position between the mucosal layer L and the muscular layer P so that the ethanol Z is blocked at the surface of the mucosal layer L. Even if the ethanol Z has circumvented the polylactate sheet E from the surface of the mucosal layer L and infiltrated the submucosal layer N, the sodium hyaluronate solution Y injected to the position between the mucosal layer L and the muscular layer P in the protection region W suppresses penetration of the ethanol Z into the submucosal layer N in the protection region W.

In particular, because the boundary between the bulged portion L1, in which the surface of the mucosal layer L is bulged due to the sodium hyaluronate solution Y, and the flat portion L2 that does not bulge is coated with the polylactate sheet E, infiltration of the ethanol Z from the surface of the mucosal layer L toward the position between the mucosal layer L and the muscular layer P can be effectively suppressed even when the ethanol Z dwells at the boundary between the bulged portion L1 and the flat portion L2.

Thus, according to the gastrointestinal-tract constricting method of this embodiment, the mucosa basal layer M in the protection region W can be more reliably and more efficiently protected from the ethanol Z, and a part of the region that extends from the gastroesophageal junction H to the cardiac part J can be constricted by constricting the desired region of the gastroesophageal junction H.

In the embodiments described above, the protection region W is formed in one place in the circumferential direction of the gastrointestinal tract; however, it suffices if a part of the region extending from the gastroesophageal junction H to the cardiac part J can be appropriately constricted by the tissue damaged by the ethanol Z in the target region R while preventing the damage on the mucosa basal layer M over the entire region in the circumferential direction of the gastrointestinal tract inflicted by the ethanol Z supplied to the target region R. For example, the protection region W may be formed at two or more places in the circumferential direction of the gastrointestinal tract.

Although ethanol Z is described as an example of the medical substance in the embodiments described above, the medical substance may be any substance that impairs the normal functions of cells, in other words, any substance that can damage cells, and examples thereof include, in addition to ethanol Z, peptase, protease, acetylcysteine, and sodium 2-mercaptoethanesulfonate.

Moreover, although the sodium hyaluronate solution Y is described as an example of the protection substance in the first embodiment and the second embodiment, the protection substance may be any liquid that does not damage the mucosa basal layer M, that does not easily spread in the submucosal layer N, and that dwells at the site. Examples of the protection substance other than the sodium hyaluronate solution Y include solutions that contain, as a main agent, sodium chondroitin sulfate, chitosan, poly-N-acetylglucosamine, carboxymethylcellulose sodium, carmellose sodium, cyanoacrylate, and the like.

Among these medical substances and the protection substances, for example, a combination of substances that are immiscible with each other, such as a combination of the ethanol Z and the sodium hyaluronate solution Y described above, may be used.

Although embodiments of the present invention are described in detail with reference to the drawings in the description above, specific features are not limited to these embodiments, and include design modifications etc., within the scope of the present invention. For example, the present invention is not limited to implementations in the embodiments and modifications described above but may be applied to embodiments in which these embodiments and modifications are appropriately combined, without specific limitation.

Although in the embodiments described above, the case in which the gastrointestinal-tract constricting method is applied to the treatment of gastroesophageal reflux disease is described, it suffices if the medical substance is supplied to the target region R of the gastrointestinal tract and the gastrointestinal tract can be constricted by using the constrictive effect of the tissue around the target region R undergoing formation of scars as the damaged tissue heals. Thus, the application range is not limited to the treatment of gastroesophageal reflux disease and the site to be applied is not limited to the gastroesophageal junction H.

The following invention is derived from the embodiments described above.

An aspect of the present invention provides a gastrointestinal-tract constricting method that comprises: while observing the gastrointestinal tract with an endoscope inserted into the gastrointestinal tract, placing a protection substance, which does not damage tissue, in at least one of a region between the mucosal layer and muscular layer of the gastrointestinal tract and a region in a mucosal surface of the mucosal layer so as to form a protection region that protects the mucosa basal layer from a medical substance that damages the tissue; and after forming the protection region, supplying the medical substance to a mucosal surface in a target region, which is at a position different from the protection region in a circumferential direction of the gastrointestinal tract, or to a position between the mucosal layer and the muscular layer in the target region.

According to this aspect, the gastrointestinal tract can be constricted by supplying a medical substance to a mucosal surface in the target region in the gastrointestinal tract or to a position between the mucosal layer and the muscular layer so as to damage the mucosa basal layer in the target region and by utilizing the constrictive effect of the tissue around the target region undergoing the process of forming scars as the damaged tissue heals.

In this case, since the mucosa basal layer in the target region is damaged by the medical substance, the invasiveness is low and the procedure is easy compared to the case in which the tissue is damaged by incision of the gastrointestinal tract.

Moreover, since the protection region is formed at a position different from the target region in the circumferential direction of the gastrointestinal tract before the medical substance is supplied, the mucosa basal layer in the protection region can be protected from the medical substance even when the medical substance supplied to the target region spreads in the circumferential direction of the gastrointestinal tract beyond what is necessary. In this manner, excessive constriction of the gastrointestinal tract by damaging the mucosa basal layer throughout the entire region in the circumferential direction of the gastrointestinal tract can be prevented.

Thus, the gastrointestinal tract can be constricted by constricting the desired region of the gastrointestinal tract by a simple and low-invasiveness procedure.

In the aspect described above, the protection substance may have a higher viscosity than the medical substance.

When the protection substance has a higher viscosity than the medical substance, the protection substance does not spread easily in the circumferential direction of the gastrointestinal tract compared to the medical substance, and, thus, the protection region can be easily and accurately formed in the desired region.

In the aspect described above, the protection substance may be sodium hyaluronate and the medical substance may be ethanol.

Since sodium hyaluronate and ethanol are sparingly miscible with each other, the mucosa basal layer in the protection region can be more reliably protected from the medical substance by using sodium hyaluronate as the protection substance and ethanol as the medical substance.

In the aspect described above, after the protection region that protects the mucosa basal layer in the region between the mucosal layer and the muscular layer of the gastrointestinal tract is formed, the mucosal surface in the protection region may be coated with the protection substance so as to prevent infiltration of the medical substance into a position between the mucosal layer and the muscular layer from the mucosal surface in the protection region; and after the mucosal surface in the protection region is coated, the medical substance may be supplied to the mucosal surface in the target region.

The protection region can be formed without damaging the tissue in the mucosal surface by a more simple procedure that involves coating the mucosal surface in the protection region with the protection substance. Moreover, the mucosa basal layer in the target region can be damaged to cause constriction by infiltration of the medical substance into the position between the mucosal layer and the muscular layer by a simple procedure of simply supplying the medical substance onto the mucosal surface in the target region.

In this case, because the mucosal surface in the protection region is coated, infiltration of the medical substance into the position between the mucosal layer and the muscular layer can be blocked at the mucosal surface even when the medical substance penetrates the mucosal surface in the protection region. Moreover, since the protection region is formed in advance in the region between the mucosal layer and the muscular layer, penetration of the ethanol Z into the region between the mucosal layer and the muscular layer in the protection region can be suppressed even if the medical substance has circumvented the mucosal surface in the protection region and penetrated the region between the mucosal layer and the muscular layer. Thus, the mucosa basal layer in the protection region can be efficiently protected.

In the aspect described above, the protection region and the target region may be formed in the gastroesophageal junction where the stomach and the esophagus connect.

The gastroesophageal junction can be constricted by a simple and low-invasiveness procedure by forming the protection region and the target region in the gastroesophageal junction.

In the aspect described above, the protection region may be formed within a range smaller than the target region in the circumferential direction of the gastrointestinal tract.

When the protection region is formed within a range smaller than the target region in the circumferential direction of the gastrointestinal tract, the constrictive effect can be generated in the mucosa basal layer over a wide range in the circumferential direction of the gastrointestinal tract without excessively constricting the gastrointestinal tract; and, thus, the gastrointestinal tract can be appropriately constricted.

REFERENCE SIGNS LIST 1 endoscope
E polylactate sheet (protection substance)
R target region
W protection region
Y sodium hyaluronate solution (protection substance, other protection substance)
Z ethanol (medical substance)

The invention claimed is:

1. A method for constricting a lumen in a gastrointestinal tract, the method comprising:
    while observing the gastrointestinal tract with an endoscope inserted into the gastrointestinal tract, placing a protection substance, which does not damage tissue, in at least one of a region between a mucosal layer and a muscular layer of the gastrointestinal tract and a region in a mucosal surface of the mucosal layer so as to form a protection region that protects a mucosa basal layer from a medical substance that damages the tissue; and
    subsequent to the forming of the protection region, supplying the medical substance to a mucosal surface in a target region or to a position between the mucosal layer and the muscular layer in the target region, the target region being at a position different from the protection region in a circumferential direction of the gastrointestinal tract, the protection substance not being placed in the target region.

2. The gastrointestinal tract constricting method according to claim 1, wherein the protection substance has a higher viscosity than the medical substance.

3. The gastrointestinal tract constricting method according to claim 1, wherein the protection substance is in the region between the mucosal layer and the muscular layer of the gastrointestinal tract and is sodium hyaluronate and the medical substance is ethanol.

4. The gastrointestinal tract constricting method according to claim 1, further comprising:
    confirming that a part of a region extending from a gastroesophageal junction to a cardiac part is in a constricted state with the endoscope inserted into the gastrointestinal tract,
    wherein the protection region and the target region are in the gastroesophageal junction where a stomach and an esophagus connect.

5. The gastrointestinal tract constricting method according to claim 1, wherein the placing forms the protection region within a range smaller than the target region in the circumferential direction of the gastrointestinal tract.

6. The gastrointestinal tract constricting method according to claim 1, wherein the supplying of the medical substance supplies the medical substance at multiple positions, each different from the protection region.

7. The gastrointestinal tract constricting method according to claim 1, wherein the protection substance comprises a first protection substance and the placing comprises placing the first protection substance in the region between the mucosal layer and the muscular layer, the method further comprises coating the region in the mucosal surface of the mucosal layer with a second protection substance, the placing and coating forming the protection region so as to prevent infiltration of the medical substance into a position between the mucosal layer and the muscular layer from the mucosal surface in the protection region, subsequent to the placing and the coating, the supplying of the medical substance supplies the medical substance to the mucosal surface in the target region or to the position between the mucosal layer and the muscular layer in the target region, and
neither the placing nor the coating are performed in the target region.

8. The gastrointestinal tract constricting method according to claim 7, wherein the coating of the region in the mucosal surface is performed subsequent to the placing.

9. A method for constricting a lumen in a gastrointestinal tract, the method comprising:
while observing the gastrointestinal tract with an endoscope inserted into the gastrointestinal tract, coating a region in a mucosal surface of a mucosal layer of the gastrointestinal tract with a protection substance, which does not damage tissue, so as to form a protection region that protects a mucosa basal layer from a medical substance that damages the tissue; and
subsequent to the coating, supplying the medical substance to a mucosal surface in a target region or to a position between the mucosal layer and a muscular layer in the target region, the target region being at a position different from the protection region in a circumferential direction of the gastrointestinal tract, the target region not being coated with the protection substance.

10. The gastrointestinal tract constricting method according to claim 9, wherein the protection substance has a higher viscosity than the medical substance.

11. The gastrointestinal tract constricting method according to claim 9, wherein the protection substance is polylactate and the medical substance is ethanol.

12. The gastrointestinal tract constricting method according to claim 9, further comprising:
confirming that a part of a region extending from a gastroesophageal junction to a cardiac part is in a constricted state with the endoscope inserted into the gastrointestinal tract,
wherein the protection region and the target region are in the gastroesophageal junction where a stomach and an esophagus connect.

13. The gastrointestinal tract constricting method according to claim 9, wherein the coating forms the protection region within a range smaller than the target region in the circumferential direction of the gastrointestinal tract.

14. The gastrointestinal tract constricting method according to claim 9, wherein the protection substance is placed between one portion of the medical substance and another portion of the medical substance in the circumferential direction of the gastrointestinal tract.

15. A method for constricting a lumen in a gastrointestinal tract, the method comprising:
while observing the gastrointestinal tract with an endoscope inserted into the gastrointestinal tract, placing a protection substance, which does not damage tissue, in a region between a mucosal layer and a muscular layer of the gastrointestinal tract so as to form a protection region that protects a mucosa basal layer from a medical substance that damages the tissue;
subsequent to the placing, supplying the medical substance to a mucosal surface in a target region or to a position between the mucosal layer and the muscular layer in the target region, the target region being at a position different from the protection region in a circumferential direction of the gastrointestinal tract, the protection substance not being placed in the target region; and
bringing the medical substance in contact with the protection substance in the circumferential direction of the gastrointestinal tract.

16. The gastrointestinal tract constricting method according to claim 15, wherein the protection substance has a higher viscosity than the medical substance.

17. The gastrointestinal tract constricting method according to claim 15, wherein the protection substance is sodium hyaluronate and the medical substance is ethanol.

18. The gastrointestinal tract constricting method according to claim 15, further comprising:
confirming that a part of a region extending from a gastroesophageal junction to a cardiac part is in a constricted state with the endoscope inserted into the gastrointestinal tract,
wherein the protection region and the target region are in the gastroesophageal junction where a stomach and an esophagus connect.

19. The gastrointestinal tract constricting method according to claim 15, wherein the placing forms the protection region within a range smaller than the target region in the circumferential direction of the gastrointestinal tract.

20. The gastrointestinal tract constricting method according to claim 15, wherein the protection substance is placed between one portion of the medical substance and another portion of the medical substance in the circumferential direction of the gastrointestinal tract.

* * * * *